(12) United States Patent
Kim et al.

(10) Patent No.: US 11,744,461 B2
(45) Date of Patent: Sep. 5, 2023

(54) RETINA IMAGING METHOD AND DEVICE, AND RETINA AND OPTIC NERVE FUNCTION EVALUATION SYSTEM

(71) Applicants: KOREA INSTITUTE OF SCIENCE AND TECHNOLOGY, Seoul (KR); SEOUL NATIONAL UNIVERSITY HOSPITAL, Seoul (KR); Inha University Research and Business Foundation, Incheon (KR)

(72) Inventors: Jae Hun Kim, Seoul (KR); Dae Yu Kim, Incheon (KR); Seok Hwan Kim, Seoul (KR); Youngho Cho, Seoul (KR); Byeongho Park, Seoul (KR); Hyo-suk Kim, Seoul (KR); Subeen Park, Seoul (KR); Kyoung Min Lee, Seoul (KR)

(73) Assignees: KOREA INSTITUTE OF SCIENCE AND TECHNOLOGY, Seoul (KR); SEOUL NATIONAL UNIVERSITY HOSPITAL, Seoul (KR); INHA UNIVERSITY RESEARCH AND BUSINESS FOUNDATION, Incheon (KR)

( * ) Notice: Subject to any disclaimer, the term of this patent is extended or adjusted under 35 U.S.C. 154(b) by 655 days.

(21) Appl. No.: 16/801,604

(22) Filed: Feb. 26, 2020

(65) Prior Publication Data
US 2020/0367747 A1    Nov. 26, 2020

(30) Foreign Application Priority Data

May 21, 2019    (KR) .......................... 10-2019-0059409

(51) Int. Cl.
A61B 3/14    (2006.01)
G06T 7/00    (2017.01)
(Continued)

(52) U.S. Cl.
CPC .............. *A61B 3/14* (2013.01); *G02B 21/0032* (2013.01); *G02B 21/365* (2013.01); *G06T 7/0012* (2013.01); *G06T 2207/30041* (2013.01)

(58) Field of Classification Search
CPC .... G02B 21/00; G02B 21/36; G02B 21/0032; G02B 21/025; G02B 21/365; G02B 15/14;
(Continued)

(56) References Cited

U.S. PATENT DOCUMENTS

| 8,480,232 B2 | 7/2013 | Aikawa |
| 9,320,424 B2 | 4/2016 | Imamura |

(Continued)

FOREIGN PATENT DOCUMENTS

| JP | 2013111421 A | 6/2013 |
| JP | 2015165785 A | 9/2015 |

(Continued)

OTHER PUBLICATIONS

Zhuolin Liu et al., "Imaging and quantifying ganglion cells and other transparent neurons in the living human retina," PNAS, Nov. 2017, pp. 12803-12808, vol. 114, No. 48.

*Primary Examiner* — Jie Lei
(74) *Attorney, Agent, or Firm* — CANTOR COLBURN LLP

(57) ABSTRACT

The present disclosure relates to a retina imaging method in which a light from a light source into two lights is dispersed, at least one eyeground image of the eyeball at a first magnification is obtained by adjusting the paths of the two lights incident on the eyeball, and a plurality of DIC images are obtained at a second magnification higher than the first magnification with respect to the retina of the entirety of the obtained at least one eyeground image by adjusting the paths of the two lights incident on the eyeball.

6 Claims, 9 Drawing Sheets

(51) Int. Cl.
*G02B 21/00* (2006.01)
*G02B 21/36* (2006.01)

(58) Field of Classification Search
CPC .. G02B 26/06; A61B 3/10; A61B 3/12; A61B 3/14; A61B 3/103; A61B 3/145; A61B 3/0008; A61B 5/7275; A61B 5/7267; G06T 7/00; G06T 7/0012; G06T 7/0016; G06T 2207/30041; G06T 2207/20081
USPC ............... 351/206, 205, 208, 210, 221, 246; 359/656, 666, 661, 422, 689
See application file for complete search history.

(56) References Cited

U.S. PATENT DOCUMENTS

| | | | |
|---|---|---|---|
| 9,420,951 | B2 | 8/2016 | Yonezawa |
| 10,130,254 | B2 | 11/2018 | Kim et al. |
| 10,383,516 | B2 | 8/2019 | Sakagawa |
| 10,416,433 | B2 | 9/2019 | Matsumoto |
| 2001/0033428 | A1* | 10/2001 | Ohno .................. G02B 15/177 359/689 |
| 2007/0236659 | A1* | 10/2007 | Yamaguchi ............ A61B 3/103 351/205 |
| 2008/0165322 | A1 | 7/2008 | Su et al. |
| 2014/0121530 | A1* | 5/2014 | Kim ....................... A61B 3/145 600/476 |
| 2017/0247613 | A1 | 8/2017 | Ono |
| 2017/0266041 | A1 | 9/2017 | Kim et al. |
| 2019/0313901 | A1 | 10/2019 | Kwon et al. |

FOREIGN PATENT DOCUMENTS

| | | |
|---|---|---|
| JP | 6114495 B2 | 4/2017 |
| JP | 6128841 B2 | 5/2017 |
| JP | 6433507 B2 | 12/2018 |
| KR | 101447005 B1 | 10/2014 |
| KR | 1020160130155 A | 11/2016 |
| KR | 101712738 B1 | 3/2017 |
| KR | 101814444 B1 | 1/2018 |
| KR | 101817000 B1 | 1/2018 |
| KR | 101855298 B1 | 5/2018 |
| KR | 101856753 B1 | 5/2018 |
| KR | 101874778 B1 | 8/2018 |
| KR | 1020190005485 A | 1/2019 |

* cited by examiner

RETINA IMAGING METHOD AND DEVICE, AND RETINA AND OPTIC NERVE FUNCTION EVALUATION SYSTEM

CROSS-REFERENCE TO RELATED APPLICATION

This application claims priority to and the benefit of Korean Patent Application No. 10-2019-0059409 filed in the Korean Intellectual Property Office on May 21, 2019, the entire contents of which are incorporated herein by reference.

BACKGROUND OF THE INVENTION

(a) Field of the Invention

The present invention relates to a retina imaging method, a device therefor, and a retina and optical nerve function evaluation system, and more particularly, to a retina and optical nerve function evaluation system that can construct a density map of retinal ganglion cells by photographing a retina image.

(b) Description of the Related Art

Central nervous system cells are no longer able to be divided and regenerated after a certain time after birth. Thus, when the central nervous system cells associated with vision are lost, they are not restored and cause progressive visual impairment, which in some cases leads to blindness. Such loss of the nerve cell is observed in various congenital retina diseases (retina pigment epithelial degeneration, hepatic or vertebral dystrophy, Stargardt disease, etc.), acquired retina diseases (macular degeneration and diabetic retinopathy) or optic nerve diseases (optic neuritis, ischemic optic neuropathy, Leber congenital melanoma, etc.) and glaucoma. Among them, glaucoma causes progressive visual field disorder due to persistent loss of retinal ganglion cells and occupies the second cause of blindness in the world as a single disease.

Currently, a method of inspecting retina and optic nerve functions uses a visual field test and an ophthalmic optical tomography inspection (OCT inspection). The visual field test is a method of determining the field of vision by measuring the threshold of light that can be identified at each point of the retina using an automated static perimetry. This visual field measurement has problems in that its result may vary depending upon the degree of cooperation of the subject, resulting in poor objectivity and reproducibility between inspections as well as it takes about 20 minutes or more when binocular inspection is performed.

Further, an optical coherence tomography inspection examines the appearance of an eyeball by tomography of the eyeball and infers the distribution of retinal ganglion cells indirectly based on the thickness of the retinal layer. A change in the thickness of the retinal ganglion cell is observed at the state that the cell loss due to disease has been progressed beyond a predetermined stage. That is, there is a problem in that the optical coherence tomography is not suitable for identifying early cellular changes by retinal diseases.

Therefore, there is a need for a system and method capable of more directly and objectively evaluating the retina and optic nerve functions and early diagnoses of the retinal disease.

The above information disclosed in this Background section is only for enhancement of understanding of the background of the invention and therefore it may contain information that does not form the prior art that is already known in this country to a person of ordinary skill in the art.

SUMMARY

The present invention has been made in an effort to provide a retina and optic nerve function evaluation system which can improve objectivity and inter-inspection reproducibility regardless of the coordination of subject in the retina and optic nerve function evaluation, shorten the time required for the function evaluation and early diagnoses of the retina and optic nerve-related diseases.

An exemplary embodiment of the present invention provides a retina and optic nerve function evaluation system including: a retina imaging unit for obtaining a plurality of differential interference contrast (DIC) images for at least a portion of the eyeball to generate a retina image; and a cell density distribution generation unit for identifying at least retinal ganglion cell and horizontal cell in the retina image and generating a density distribution map of the retinal ganglion cell which represents at least the distribution of the retinal ganglion cell.

The retina imaging unit may obtain at least one eyeground image corresponding to at least a portion of the eyeball at low magnification and obtain a plurality of DIC images of the retina of the entirety of the obtained at least one eyeground image.

The cell density distribution generation unit may classify the retinal ganglion cell and the horizontal cell in consideration of the size and shape of the cell in the retina image.

The cell density distribution generation unit may divide the retina image into a subpixel having a predetermined size, classify a cell larger than the subpixel as a retinal ganglion cell and classify a cell smaller than the subpixel as an horizontal cell.

The cell density distribution generation unit may select the horizontal cell by observing a change in the shade of the boundary region of the horizontal cell.

The retina imaging unit may include a light irradiation unit for irradiating two lights dispersed in the eyeball, a magnification adjustment unit for making the two lights incident on the eyeball by adjusting the paths of the two lights, and a light compensation unit for receiving a light reflected from the eyeball and compensating for the aberration of the light generated in the eyeball.

The retina and optic nerve function evaluation system may further include a data storage unit for storing the retina image and a cell density distribution map of the retinal ganglion, and a function information generation unit for generating retina and optic nerve function information by analyzing the retina image and the cell density distribution map of the retinal ganglion.

Another exemplary embodiment of the present invention provides a retina imaging device including: a light irradiation unit for irradiating two dispersed lights; a magnification adjustment unit for adjusting the magnification of an image obtained from the two lights incident on the eyeball by adjusting the paths of the two lights; a light compensation unit for receiving a light reflected from the eyeball and compensating for the aberration of light generated in the eyeball; and a light processing unit for obtaining a DIC image based on an electrical signal of the compensated reflected light. The retina imaging device may obtain at least one eyeground image at a first magnification, and obtain a plurality of DIC images at a second magnification higher than the first magnification with respect to the retina of the entirety of the obtained at least one eyeground image.

The magnification adjustment unit may include a first lens on which the two dispersed lights are incident; a second lens on which the two lights that have passed through the first lens are incident; and a third lens on which the two lights that have passed through the second lens are incident. The magnification adjustment unit can adjust the magnification according to the movement of the third lens.

The magnification adjustment unit may further include a fixed frame to which the first lens and the second lens are fixed; and an adjustment frame to which the third lens is fixed and whose position is moved with respect to the fixed frame.

The position of the third lens at the first magnification may be farther from the eyeball than the position of the third lens at the second magnification.

At the first magnification, a region corresponding to the at least one eyeground image is specified by the two lights that have passed through the third lens and the lens of the eyeball, and at the second magnification, a specific point of the region corresponding to at least one eyeground image obtained by the two lights that have passed through the third lens and the lens of the eyeball may be specified.

The light irradiation unit may include a differential interference contrast (DIC) prism for dispersing a light to produce the two dispersed lights.

The two lights reflected from the eyeball are combined into one light in the DIC prism through the magnification adjustment unit and incident on the light compensation unit. The light compensation unit may include a wavefront sensor for detecting the aberration of the incident light, and a variable mirror which is adjusted by the wavefront sensor for compensating for the aberration of the incident light.

Yet another exemplary embodiment of the present invention provides a retina imaging method using a DIC microscope, the method including: dispersing a light from a light source into two lights; obtaining at least one eyeground image of an eyeball at a first magnification by adjusting the paths of the two lights incident on the eyeball; and obtaining a plurality of DIC images at a second magnification higher than the first magnification with respect to the retina of the entirety of the obtained at least one eyeground image by adjusting the paths of the two lights incident on the eyeball.

The retina imaging method may further include receiving a light reflected from the eyeball to compensate for the aberration of light generated in the eyeball; and generating the at least one eyeground image or the plurality of DIC images based on the compensated reflected light.

The at least one eyeground image may be an image for a region of the retina specified between the two lights, and each of the plurality of DIC images may be an image for a plurality of specific points in the region of the specified retina.

The retina and optic nerve function evaluation system according to an exemplary embodiment of the present invention may generate a retina image by scanning a retina; and generate a density distribution map of a retinal ganglion cell of the retina based on the retina image.

That is, direct observation of the retinal ganglion cell is possible, and by confirming its density distribution, it is possible to make an objective evaluation of how much damage is caused to which portion when a retinal and optic nerve disease occurs, and through this, evaluation of the retina and optic nerve function can be performed.

The retina image is generated by photographing the retina of the subject, and its generation process is temporary and does not directly affect the human body.

Further, the retina image can be generated precisely enough to visually distinguish the retinal ganglion cell from other cells, and its density distribution map is automatically generated: even though a high level of medical instructions or experience from a physician and the like is required, retina and optic nerve function evaluation information can still be easily provided to the subject.

DETAILED DESCRIPTION

Figure 1:
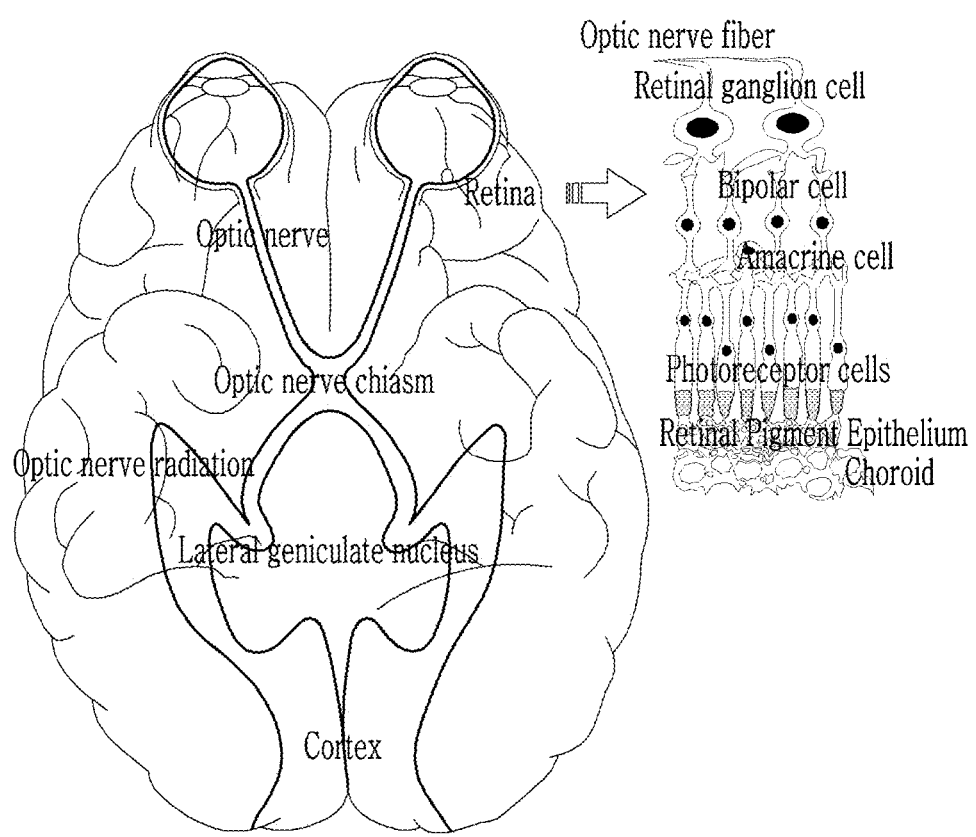
FIG. 1 is a view of a structure of a retina and an optic nerve.

According to an exemplary embodiment, a retinal ganglion cell (RGC) can be directly measured to build-up a retinal ganglion cell map, thereby providing a more objective and accurate retina and optic nerve function evaluation system and a method of outputting its information. In this case, an image for an eyeground region of the retina and a specific point in the eyeground region may be obtained through magnification adjustment, and the image for the specific point may be a differential interference contrast (DIC) image. The DIC image may refer to an image which is obtained through a DIC microscope.

Hereinafter, exemplary embodiments disclosed herein will be described in detail with reference to the accompanying drawings in which the same or similar components will be given the same or similar reference numerals and overlapping description thereof will be omitted. The suffixes "module" and/or "unit" for constituent elements used in the following description are given or used in consideration of ease of specification draft, and do not have distinct meanings or roles from each other. Further, in describing the exemplary embodiments disclosed herein, if it is determined that the detailed description of the related well-known technologies may obscure the gist of the exemplary embodiments disclosed herein, the detailed description thereof will be omitted. In addition, it should be understood that the accompanying drawings are only for easily understanding the exemplary embodiments disclosed herein, do not limit the technical spirit disclosed in the specification with reference to the accompanying drawings and cover all changes, equivalents and substitutes included in the spirit and scope of the present invention.

Terms including ordinal numbers such as a first, a second, etc. may be used to describe various constituent elements, but the constituent elements are not limited by the terms. The terms are used only for the purpose of distinguishing one constituent element from another.

It should be understood that in this application, the terms "comprises" or "includes" are intended to indicate that there is a feature, number, step, operation, constituent element, part, or combination thereof described in the specification, and do not exclude in advance the possibility of the presence or the addition of one or more other features, numbers, steps, operations, constituent elements, parts, or a combination thereof.

FIG. 1 is a view showing a structure of a retina and optic nerve.

The human eye has a structure similar to a camera. The cornea and lens of the eye correspond to the lens of camera, the iris of the eye corresponds to the iris of camera, the retina of the eye corresponds to a camera film, and the optic nerve corresponds to an image transmission cable of digital camera. External lights are collected through the cornea, the amount of the lights is adjusted by the iris, and the thickness of the lens of the eye is adjusted so that an accurate image is focused on the retina. In this case, the damaged cornea can be restored by corneal transplantation and the cataract with the clouded lens can be restored by artificial lens, but if the retina or optic nerve is damaged once, it cannot be treated, and the vision will be lost. The retina, which is a thin layer of the nerve cells that construct an inner wall surrounding the inside of the eye, converts external light signals that enter the eye into electrical signals and transmits the electrical signals to the brain through the optic nerve.

As shown in FIG. 1, the structure of the retina is composed of a retinal ganglion cell (RGC), a bipolar cell, an horizontal cell, and a photoreceptor cell.

When the external light is focused on the retina, a light-receiving cell at the bottom of the retina converts the light signal into a bioelectric signal which can be interpreted by a nervous system. This bioelectrical signal is transmitted to the retinal ganglion cells through the bipolar cells and horizontal cells.

Optic nerve fibers starting from the retinal ganglion cell gather in an optic nerve papilla to form an optic nerve, and cross at an optic chiasm to reach a lateral geniculate nucleus. The optic nerves make a synapse in the lateral geniculate nucleus, and the bioelectrical signal is transmitted to a visual cortex through optic nerve radiation to feel the vision.

A retinal ganglion cell is a cell that performs an important function of transmitting a bioelectrical signal generated by a photoreceptor cell to the optic nerve. The loss of such retinal ganglion cell is associated with defects of the retina and optic nerve, and can be observed in various diseases such as glaucoma, optic neuropathy, optic neuritis and diabetic retinopathy. Therefore, determining the total number of retinal ganglion cells and whether the retinal ganglion cells have been damaged may be an important method for performing normal function evaluation of the retina and optic nerve.

The retina and optic nerve function evaluation system 1 according to an exemplary embodiment of the present invention can scan the retina and generate a density distribution map of the retinal ganglion cell.

That is, the direct observation of the retinal ganglion cell is possible and in accordance with the observation of the density distribution thereof, it is possible to make an objective evaluation of the extent of damage to which part of the retinal ganglion caused by the disease thereby performing the evaluation of the retina and optic nerve function. Hereinafter, a configuration of the present invention will be described in more detail.

Figure 2:
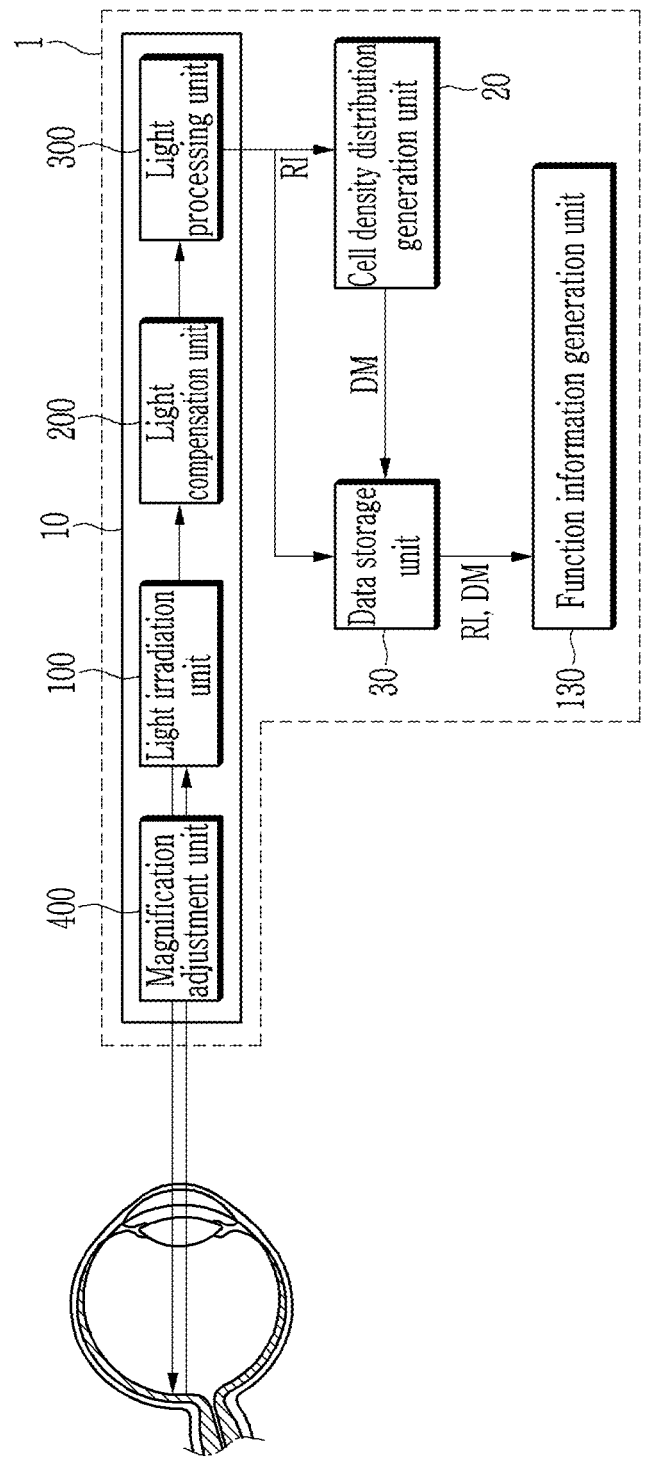
FIG. 2 is a configuration view of the retina and optic nerve function evaluation system according to an exemplary embodiment of the present invention.

FIG. 2 is a configuration view of a retina and optic nerve function evaluation system 1 according to an exemplary embodiment of the present invention.

Figure 3:
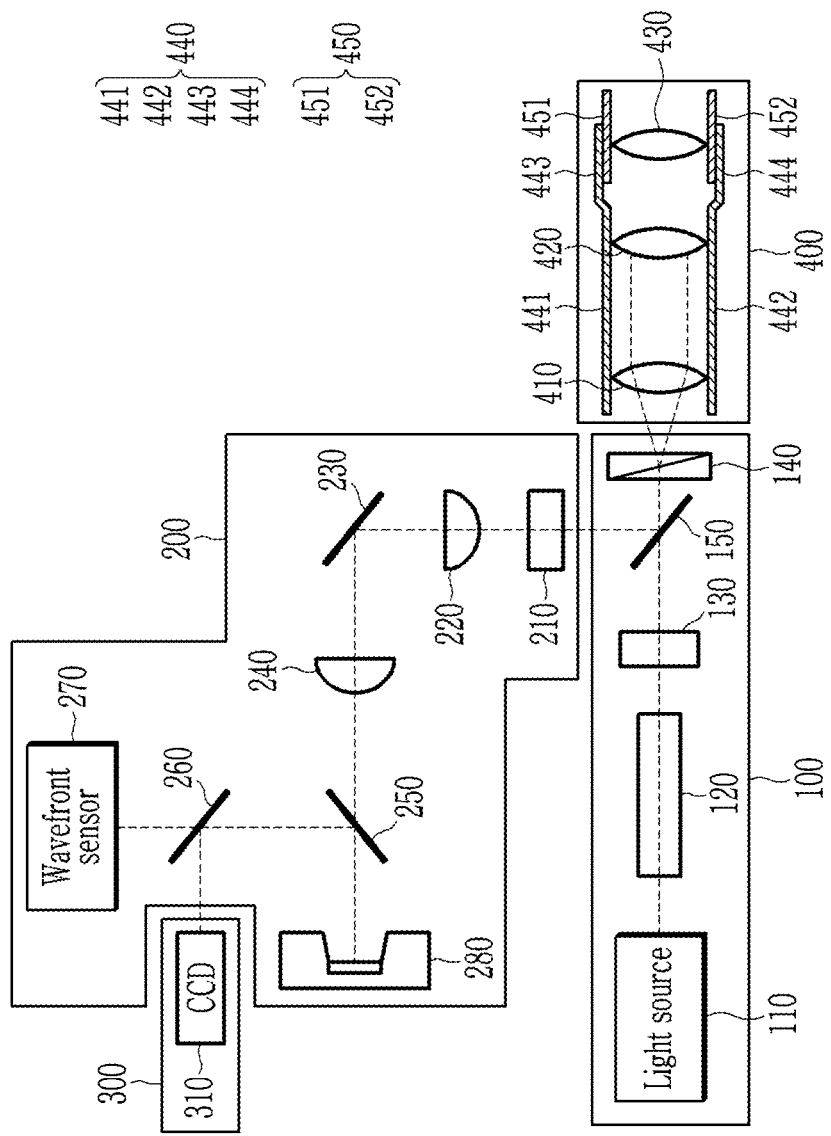
FIG. 3 is a view showing each configuration of the optic nerve function evaluation system according to an exemplary embodiment.

FIG. 3 is a view showing each configuration of the optic nerve function evaluation system according to an exemplary embodiment.

Referring to FIG. 2, the retina and optic nerve function evaluation system 1 according to an exemplary embodiment of the present invention includes a retina imaging unit 10 and a cell density distribution generation unit 20.

The retina imaging unit 10 may photograph the eyeball to generate a retina image. The retina and the cells constituting the retina are transparent and are not easy to photograph with a general photographing means.

The retina imaging unit 10 according to an exemplary embodiment of the present invention may be implemented with a differential interference contrast (DIC) microscope. The differential interference microscope can divide a light into two finely different paths and interpret the optical distance between the two lights as an interference. Accordingly, imaging of transparent cells may be possible because an imaging by an interference is possible when a difference in the optical distance occurs.

The retina imaging unit 10 may photograph at least a partial region of the retina to generate a retina image (RI).

It is possible to obtain at least one eyeground image for at least a portion of the eyeground at low magnification, obtain a DIC image of the retina by photographing the retina at a specific point in the obtained at least one eyeground image at high magnification, and obtain a DIC image of the retina of the entirety of at least one eyeground image obtained through a plane movement.

Further, the retina imaging unit 10 may observe the eyeground in real time, and may also be capable of real-time photographing the currently observed screen. In addition, the retina imaging unit 10 may generate a retina image (RI) by measuring the degree of bending of the curved retina and correcting the DIC image of the entire retina in an even state. The retina imaging unit 10 may transmit the generated retina image (RI) to a cell density distribution generation unit 20.

The retina imaging unit 10 may include a light irradiation unit 100 for irradiating lights to the eyeball and a light compensation unit 200 for compensating for the aberrations of lights generated in the eyeball by receiving the lights reflected from the eyeball, a light processing unit 300 including a CCD into which lights with a light aberration compensated are introduced, and a magnification adjustment unit 400.

The light irradiation unit 100 includes a light source 110, a Koehler illumination 120, a polarizing plate 130, a DIC prism 140, and a reflection/transmission mirror 150.

The light source 110 generates a light for imaging.

The Koehler illumination 120 generates a light supplied from the light source 110 as a sample illumination for use in the retina imaging unit 10. The sample illumination generated by the Koehler illumination 120 is an even illumination, and the even illumination is supplied to the sample so that the images of the light source 110 are not visible in the images obtained by the retina imaging unit 10. The Koehler illumination 120 may include an aperture, a lens and the like, and specific configurations and coupling relations between the configurations are well-known and detailed description thereof will be omitted.

The polarizing plate 130 transmits only a polarized light of a specific angle of the sample illumination that has passed through the Koehler illumination 120.

For example, the polarizing plate 130 may transmit only a polarized light of 45 degree.

The DIC prism 140 disperses the polarized light that has passed through the polarizing plate 130 into two lights.

The DIC prism 140 may be implemented with a Wollastone prism.

The reflection/transmission mirror 150 transmits the polarized light that has passed through the polarizing plate 130 to the DIC prism 140 and reflects the light incident from the magnification adjustment unit 400.

The magnification adjustment unit 400 may adjust the magnification of the image obtained from the two lights incident on the eyeball by adjusting the paths of two lights incident from the DIC prism 140. Then, at least one eyeground image of at least a partial region of the eyeground at a first magnification, (for example, relatively low magnification) adjusted by the magnification adjustment unit 400 may be obtained.

Next, a plurality of DIC images may be obtained with respect to the retina of the entirety of at least one eyeground image obtained at a second magnification (for example, relatively high magnification) adjusted by the magnification adjustment unit 400.

The magnification may be a ratio between the size of the image obtained through the magnification adjustment unit 400 and the photographed object.

The magnification adjustment unit 400 includes three lenses 410 to 430, a fixed frame 440, and an adjustment frame 450. Two lenses 410 and 420 are fixedly positioned inside the fixed frame 440. Two lights dispersed in the DIC prism 140 may travel through the lenses 410 and 420 along a path indicated by a dotted line in FIG. 3. For example, two lights that have passed through the lens 410 may be incident on the lens 420 in parallel with each other, and two lights that have passed through the lens 420 intersect at the focal length of the lens 420 and then may be incident on the lens 430.

The lens 430 is fixedly positioned inside the adjustment frame 450, and the position of the adjustment frame 450 may be changed with respect to the fixed frame 440.

For example, the adjustment frame 450 may move along the inner surface of the fixed frame 440.

In order to show the fixing positions of the three lenses 410, 420, 430, a cross section of the fixing frame 440 and the adjusting frame 450 is shown in FIG. 3.

Two lenses 410 and 420 are fixedly positioned between the end surfaces 441 and 442 of the fixed frame 440, and the lens 430 is fixedly positioned between the cross sections 451 and 452 of the adjustment frame 450.

The fixed frame 440 may be cylindrical as a structure for positioning the two lenses 410 and 420, and the adjusting frame 450 may be cylindrical to move along the inner surface of the fixed frame 440 as a structure for moving the lens 430.

Moving regions 443 and 444 which provide a path for the adjustment frame 450 to move in the fixed frame 440 are formed. The adjustment frame 450 may move along the moving regions 443 and 444, and a structure for movement may be formed on the outer surface of the adjustment frame 450 and the inner surface of the moving regions 443 and 444.

The structure and arrangement of the fixed frame 440 and the adjustment frame 450 as shown in FIG. 3 are only examples for describing an exemplary embodiment and the invention is not limited thereto. That is, various structures capable of moving the lens 430 to adjust the magnification may be applied.

At least one eyeground image is obtained when the magnification adjusted by the magnification adjustment unit 400 is relatively low magnification, and when the magnification adjusted by the magnification adjustment unit 400 is relatively high magnification, a plurality of DIC images of the obtained at least one eyeground image are obtained. Here, the high magnification includes a magnification range in which each of the obtained plurality of DIC images has a resolution that can be divided into cell (for example, ganglion cell) units, and the low magnification includes a magnification range capable of obtaining an eyeground image of a predetermined resolution, and the predetermined resolution can be changed depending upon a user's design.

The light irradiation unit 100 and the magnification adjustment unit 400 may move to obtain an eyeground image of a predetermined resolution with respect to the entire or partial region of the retina and may move in fine units to obtain a plurality of DIC images.

For example, the retina is divided into a plurality of regions, and the light irradiation unit 100 and the magnification adjusting unit 400 may move to have a corresponding angle at a position corresponding to each of the plurality of regions. The retina imaging unit 10 may obtain the eyeground image for all of the plurality of regions of the retina, or may obtain the eyeground image for only some of the necessary regions among the plurality of regions.

A light projected onto the eyeball through the magnification adjustment unit 400 is reflected from the retina, and the reflected light is incident on the DIC prism 140 through the magnification adjustment unit 400. In this case, the paths of the two lights reflected from the retina are the same as the incident paths and the direction may be reversed. The two lights incident on the DIC prism 140 are combined at the DIC prism 140, and the combined light is incident on the light compensation unit 200 through the reflection/transmission mirror 150.

The retina imaging unit 10 photographs the actual eyeball, and the light irradiated to the eyeball may generate aberration when passing through the lens and the cornea of the eyeball, but the aberration of the light may be compensated by the light compensation unit 200.

The optical compensation unit 200 includes an analyzer 210, lenses 220 and 240, a mirror 230, two reflection/transmission mirrors 250 and 260, a wavefront sensor 270, and a variable mirror 280.

The analyzer 210 transmits only a specific polarization of lights incident from the reflection/transmission mirror 150. For example, because the polarization angle of the polarizing plate 130 is 45 degrees, the analyzer 210 may pass only at 135 degree polarization having a 90 degree phase difference.

The lenses 220 and 240 adjust the light size, and the mirror 230 may be positioned between the lens 220 and the lens 240. The light that has passed through the analyzer 210 is enlarged while passing through the lens 220, reflected by the mirror 230 and is incident on the lens 240. The size of the light that has passed through the lens 240 may be reduced.

The variable mirror 280 includes a plurality of segments, and the plurality of segments are controlled by the wavefront sensor 270 to reduce the distortion of the wavefront to thereby improve the sensitivity and visibility of the image. The variable mirror 280 may be implemented as an adaptive mirror, a deformable mirror and the like.

The light that has passed through the lens 240 is transmitted through the reflection/transmission mirror 250 to be incident on the variable mirror 280, and the variable mirror 280 compensates and emits the incident light. The emitted lights are reflected by the reflection/transmission mirror 250.

The wavefront sensor 270 may detect the aberration of light based on the light transmitted through the reflection/transmission mirror 260 and adjust the variable mirror 280 to compensate for the aberration.

The wavefront sensor 270 may detect the aberration of light reflected from the eyeball based on the incident light and analyze the wavefront distorted by the aberration.

Specifically, the wavefront sensor 270 measures the aberration generated while the light passes through the lens of the eyeball and the lenses of the retina imaging unit 10 and adjusts each of the segments constituting the variable mirror 280 to correct the distortion of the light generated by the aberration.

The wavefront sensor 270 may linearly combine Zernike polynomial basis functions that express a wavefront aberration by comparing a reference light source used for image acquisition (that is, the light source 110 in one embodiment) and the distortion wavefront measured by the wavefront sensor 270 and reconstruct the distortion wavefront. The wavefront sensor 270 may calculate a wavefront distortion correction signal using a matrix calculation method, calculate a voltage required for driving for each segment of the variable mirror 280 for wavefront correction, and supply the calculated voltage to each segment. Then, the wavefront distortion of light entering the CCD 310 to obtain an image may be reduced.

The light compensated by the variable mirror 280 is reflected by the reflection/transmission mirror 260 and is incident on a light processing unit 300. As such, the optical compensation unit 200 is applied with correction optics (AO) to compensate for the aberration generated due to the characteristics of the eyeball, thereby enabling photographing of retinal nerve cells in vivo.

The light compensated by the light compensation unit 200 is incident on the light processing unit 300, and the light processing unit 300 includes a charge-coupled device (CCD) 310.

The CCD 310 converts the incident light into an electrical signal using a photoelectric effect, and the light processing unit 300 may convert the electrical signal outputted from the CCD 310 into a digital signal and obtain a DIC image by image-processing the digital signal. The light processing unit 300 may generate a plurality of DIC images with respect to the retina of the entirety of the obtained eyeground image and arrange the generated plurality of DIC images in the corresponding position to thereby obtain the retina image (RI) of the entirety of the obtained at least one eyeground image.

In this manner, the retina imaging unit 10 may obtain at least one eyeground image and obtain a plurality of DIC images of the retina of the entirety of the obtained at least one eyeground image. It is possible to obtain a retina image (RI) of the retina of the entirety of the thus obtained at least one eyeground image by arranging the plurality of DIC images thus obtained in the corresponding position.

Hereinafter, the operation of the magnification adjustment unit at low magnification and a high magnification will be described with reference to FIGS. 4 and 5.

Figure 4:
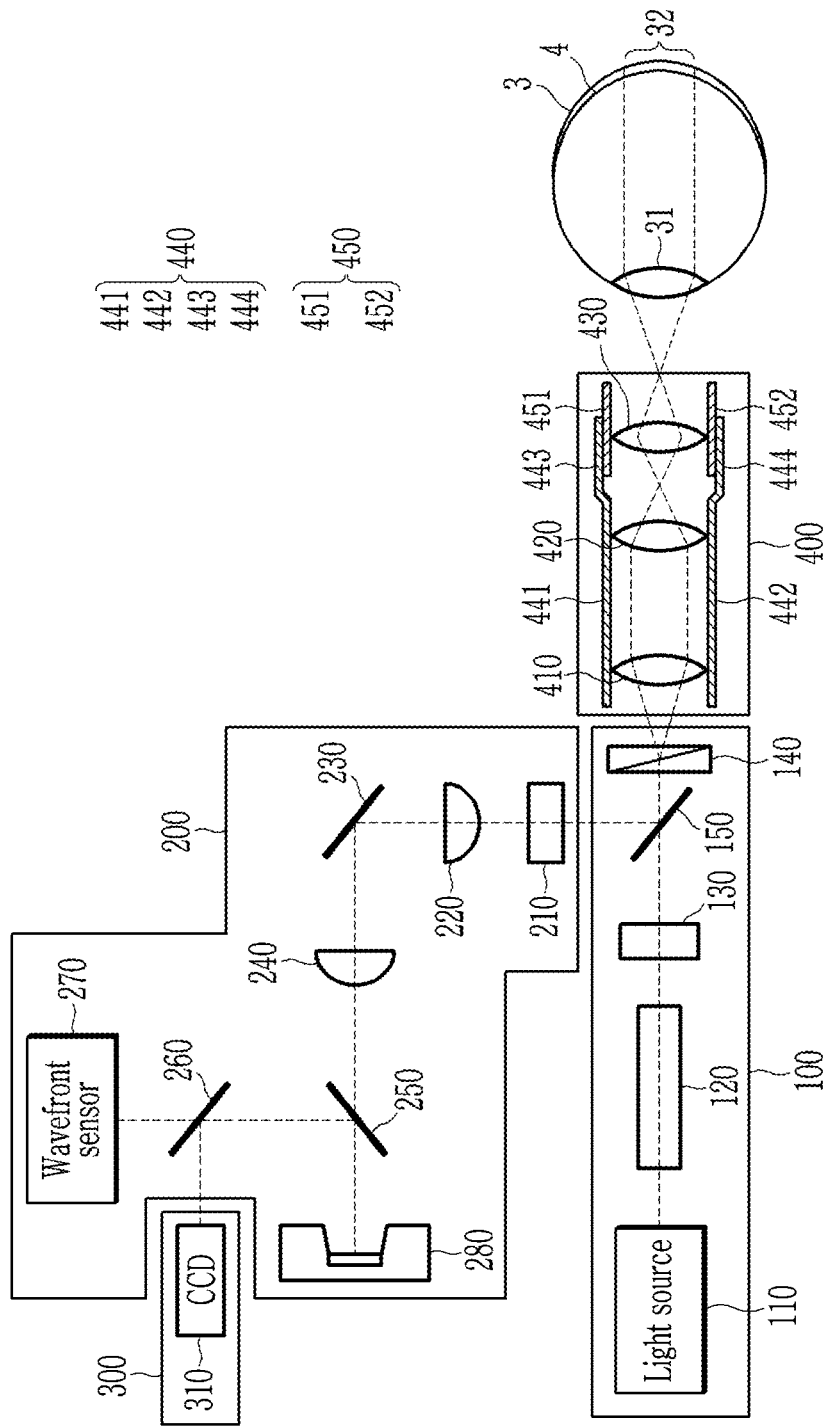
FIG. 4 is a view showing a magnification adjustment unit at low magnification according to an exemplary embodiment.

FIG. 4 is a view showing a magnification adjustment unit at low magnification according to an exemplary embodiment.

As shown in FIG. 4, the two lights that have passed through the lens (420) at low magnification travel in a crossing manner at the focal length of the lens (420), and two lights that have passed through the lens 430 travel in a crossing manner at the focal length of the lens 430 and are incident on the lens 31 of the eyeball 3. The two lights that have passed through the lens 31 of the eyeball 3 travel apart from each other and reach some regions 32 of the eyeground 4. In FIG. 4, the two lights that have passed through the lens 31 are shown to be parallel to each other, but the present invention is not limited thereto, and the two lights need to be spaced apart from each other when the two lights reached the eyeground 4 so that at least one eyeground image for some regions 32 can be obtained.

Figure 5:
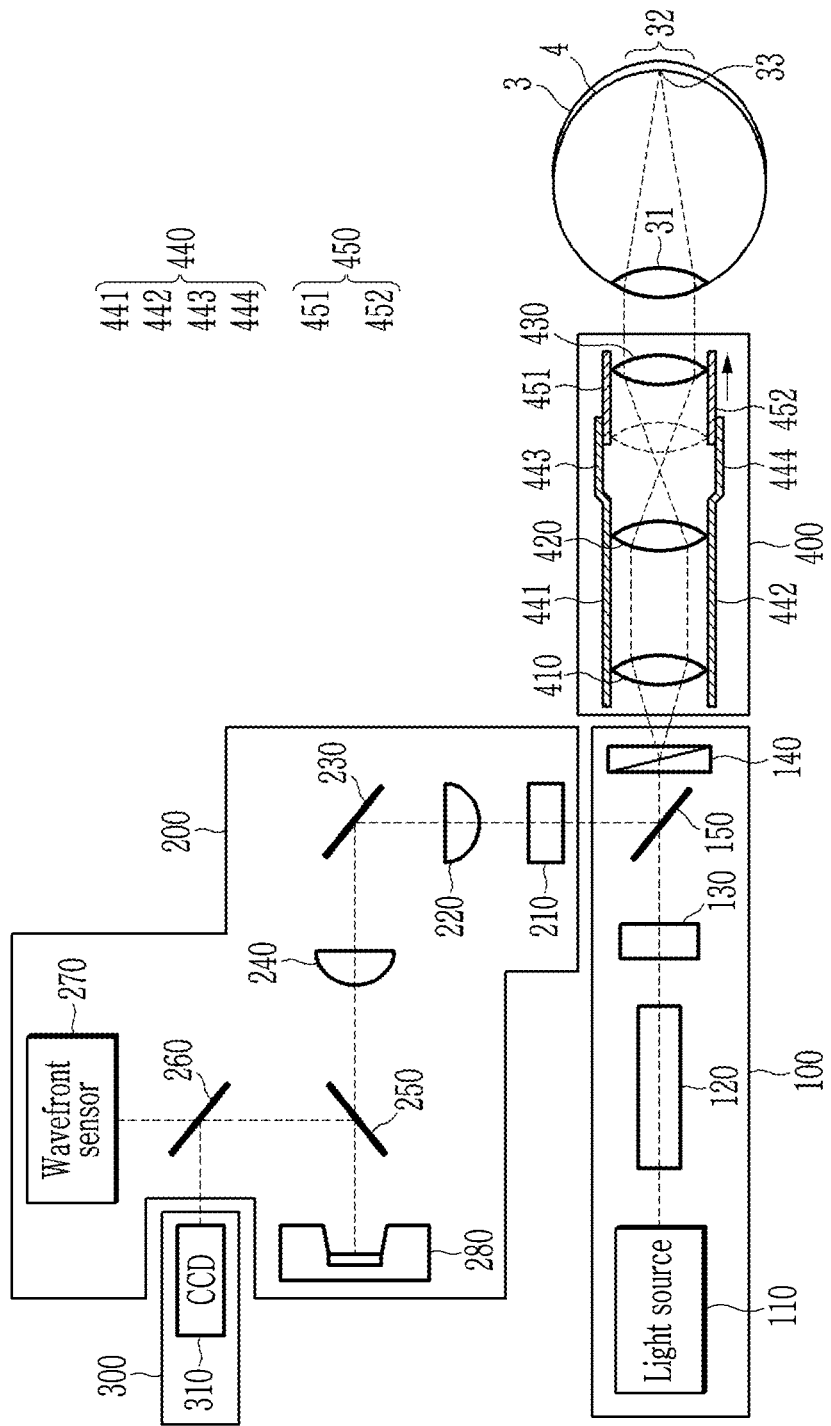
FIG. 5 is a view showing a magnification adjustment unit at high magnification according to an exemplary embodiment.

FIG. 5 is a view showing a magnification adjustment unit at high magnification according to an exemplary embodiment.

In FIG. 5, the position of the lens 430 at low magnification is shown by the dotted line.

That is, the lens 430 is moved toward the eyeball for high magnification.

The two lights that have passed through the lens 420 at high magnification travel in a crossing manner at the focal length of the lens 420, and the two lights that have passed through the lens 430 travel in parallel and are incident on the lens of the eyeball. The two lights that have passed through the lens of the eyeball reach a specific point 33 corresponding to the focal length of the lens. The specific point 33 belongs to some regions 32 of the eyeground, and a DIC image of the retina of the specific point 33 at high magnification can be obtained. The light irradiation unit 100 and the magnification adjustment unit 400 may move to change the position of the specific point 33 so that a plurality of DIC images may be obtained with respect to the entire eyeground region 32.

The two lights reflected from the eyeground region 32 of FIG. 4 and the specific point 33 of FIG. 5 travel in the reverse order of the incident path and are incident on the DIC prism 140 along the lens 31, the lens 430, the lens 420, and the lens 410. For example, the paths of the two lights that are reflected and incident on the DIC prism 140 may be the same as the incident paths and the direction may be reversed.

As such, in FIG. 5, a specific point where the two lights meet at the eyeground is obtained as a DIC image which is high magnification, while in FIG. 4, a region between the two lights, that is, a retina region having a larger size than a specific point in FIG. 5 is obtained as an image, which becomes the eyeground image of low magnification.

Figure 6:
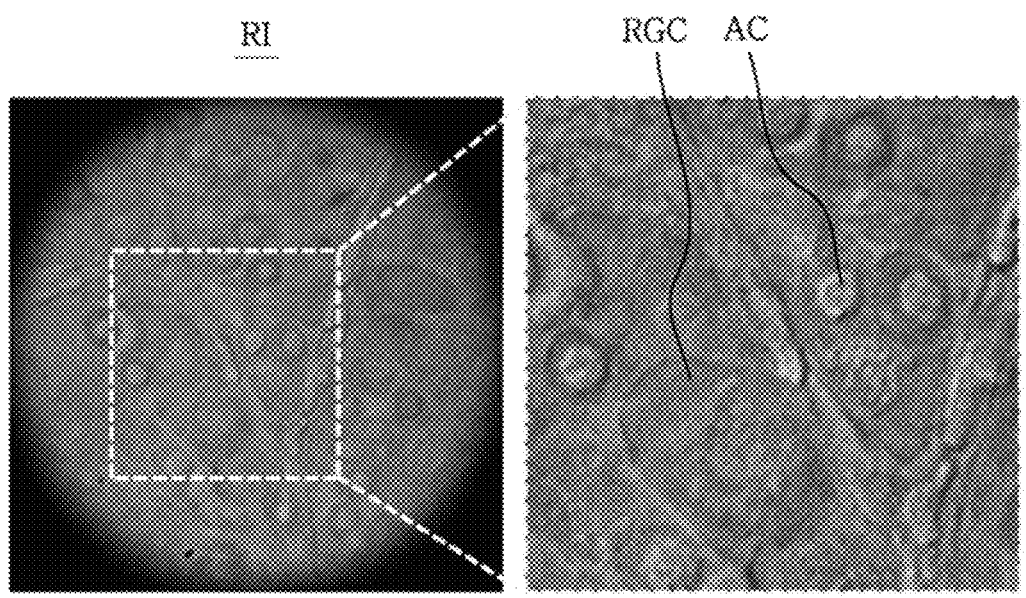
FIGS. 6 and 7 are exemplary views of retina images generated by a retina imaging unit.
Figure 7:
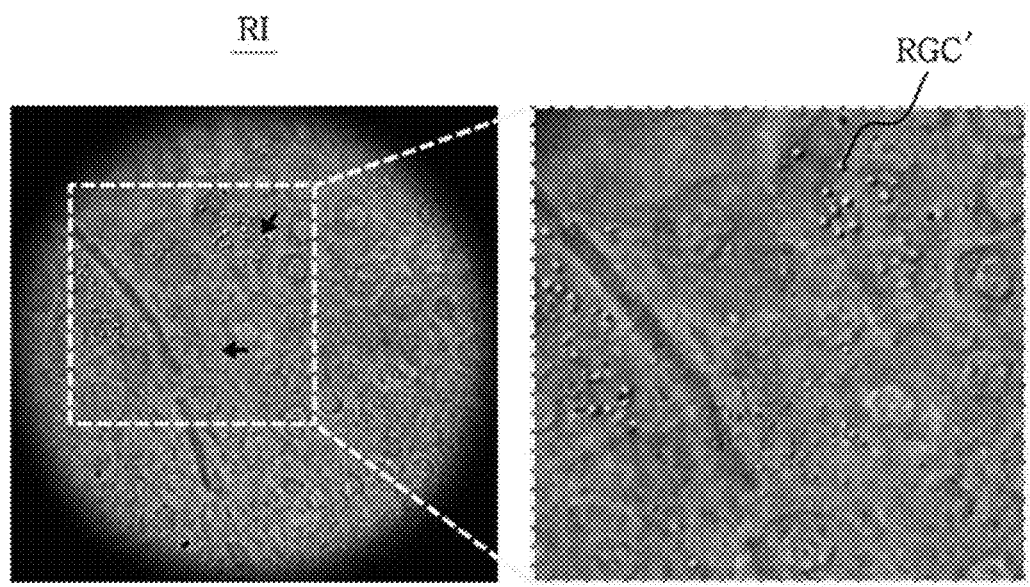
Figure 8:
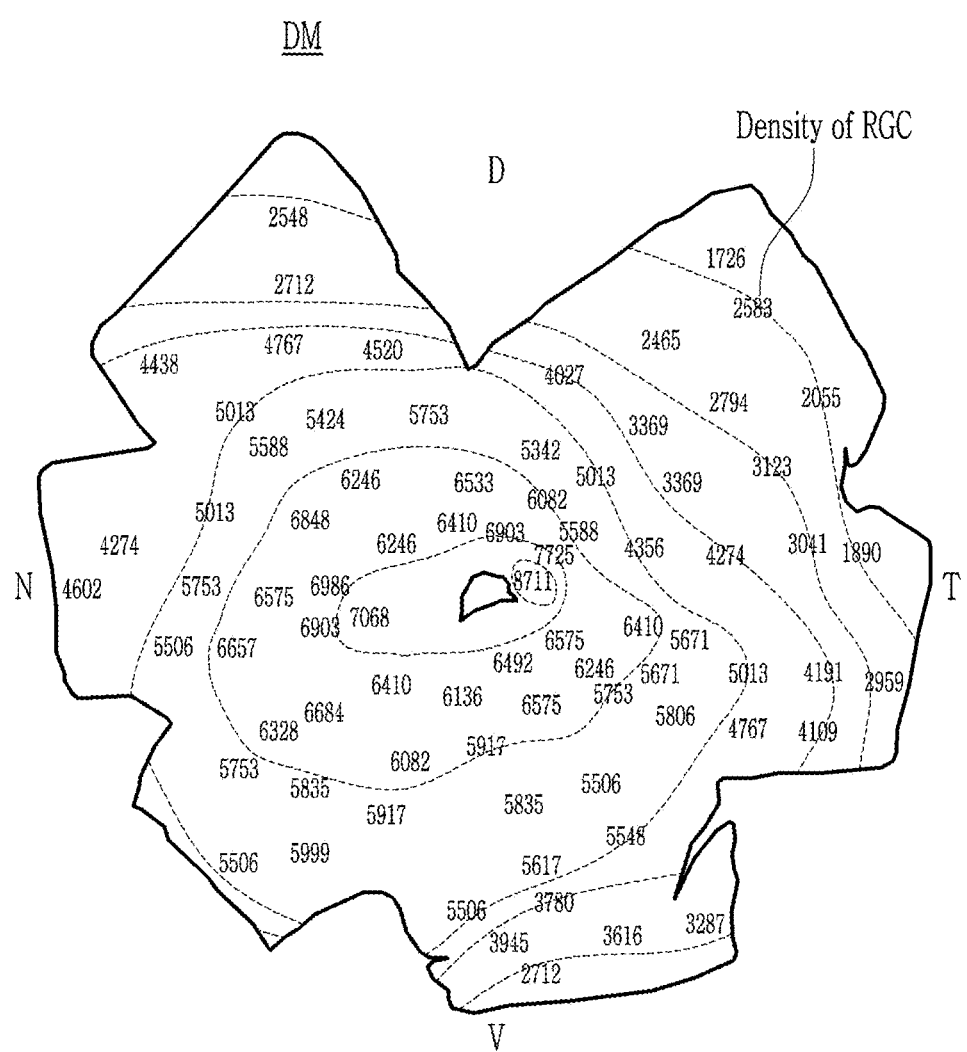
FIG. 8 is an exemplary view showing a density distribution map of a retinal ganglion cell.

FIGS. 6 and 7 are exemplary views of the retina image generated by the retina imaging unit, and FIG. 8 is an exemplary view of the density distribution map of a retinal ganglion cell.

As shown in FIG. 6, the retina image (RI) may be displayed with an optic nerve of elongated shape, horizontal cells (AC) in the shape of a gray circle surrounded by a darker gray circle, dark gray oval shaped retinal ganglion cells (RGC) and blood vessels passing between these cells.

The horizontal cells, retinal ganglion cells, and blood vessels of the retina are morphologically different from each other in terms of their function as well as their basic shape and direction of travel. The retina image (RI) of the present invention can provide a clear image so that the appearance difference of each cell of the retina can be visually identified.

As mentioned above, the distribution and density of retinal ganglion cells (RGC) are closely related to a retina disease: the cell density distribution generation unit 20 can generate a cell density distribution map (DM) that represents the distribution of retinal ganglion cell based on the provided retina image (RI).

The cell density distribution generation unit 20 may distinguish retinal ganglion cells (RGC) and horizontal cells (AC) in consideration of the size, shape, etc. of the cells in the retina image (RI).

The cell density distribution generation unit 20 may divide the retina image (RI) into a subpixel of a predetermined size, classify a cell larger than the subpixel as a retinal ganglion cell (RGC), and classify a cell smaller than the subpixels as an horizontal cell.

Further, the cell density distribution generation unit 20 may first select the horizontal cells (AC) by observing a change in the shade of the cell boundary region. That is, the horizontal cells (AC) may be selected in consideration of the fact that the edge that is the boundary region of the horizontal cells (AC) is displayed darker than the center region. The cell density distribution generation unit 20 may select a cell greater than a certain size in the remaining cells except the horizontal cells (AC) as retinal ganglion cells (RGC).

The cell density distribution generation unit 20 may select the retinal ganglion cells (RGC) and horizontal cells (AC) from the provided retina image (RI) and determine the location and number of each cell.

The cell density distribution generation unit 20 may receive a plurality of retina images (RI) from the retina imaging unit 10. The retina imaging unit 10 may photograph each portion by dividing the retina into a plurality of retinas: one retina image (RI) received by the cell density distribution generation unit 20 may be a photographed image of a specific portion of the retina.

The cell density distribution generation unit 20 may select the horizontal cells (AC) and retinal ganglion cells (RGC) included in each of the plurality of provided retina images (RI).

The plurality of selected retina images (RI) may be combined into one image representing the entire retina, and based on the combined image, a density distribution map of retinal ganglion cells showing the distribution of retinal ganglion cells (RGC) may be generated according to the retina portion. The retina image (RI) may have a certain sequence number and may be combined into one image according to the sequence number which is not limited thereto and may be combined into a single image by identifying a structure (for example, a blood vessel or the like) that is continuous between the plurality of retina images (RI).

However, the present invention is not limited thereto, and the retina image (RI) may be a photographed image of the entire retina, and the cell density distribution generation unit 20 may utilize the retina image (RI) provided by the retina imaging unit 10 to generate the density distribution map of the retinal ganglion cells.

Further, the cell density distribution generation unit 20 according to some embodiments may select the normal retinal ganglion cells and abnormal retinal ganglion cells (RGC') from the retina image (RI). Here, FIG. 7 is a view showing a retina image (RI) including the abnormal retinal ganglion cells (RGC'). Normal retinal ganglion cells do not generate abnormal states such as bubbles in the center of the cell, while it can be seen that the abnormal retinal ganglion cells generate abnormal states such as bubbles during the death of cell.

An abnormal state such as bubbles may occur in the process of the death of retinal ganglion cells (RGC) due to a variety of causes. The cell density distribution generation unit 20 may distinguish such abnormal retinal ganglion cells from normal retinal ganglion cells, and may subtract the selected abnormal retinal ganglion cells from the number of retinal ganglion cells. However, the present invention is not limited thereto, and the abnormal retinal ganglion cells may be separately reflected into the density distribution map of the retinal ganglion cells.

FIG. 8 is a view showing the density distribution map of retinal ganglion cells.

As shown in FIG. 8, the density of retinal ganglion cells may be expressed as a predetermined value in each region but is not limited thereto. The density distribution map of retinal ganglion cells can distinguish retinal ganglion cells from other cells as the color difference of each pixel in a state that the retina region has been divided into subpixels. Here, the density of retinal ganglion cells can be expressed as the color density of the pixel. The density distribution map of the retinal ganglion cells can easily determine the number of retinal ganglion cells (RGC) according to the position, and the number of these cells is calculated in a direct manner and can provide higher accuracy than an indirect diagnostic manner.

The generated density distribution map (DM) and retina image (RI) of the retinal ganglion cells may be stored in a data storage unit 30.

The retina and optic nerve function evaluation system 1 may generate a retina image (RI) and a density distribution map of ganglion cells according to a predetermined time period, and the generated data may be stored in the data storage unit 30.

For example, once a year, a regular examination may be performed to generate a retina image (RI) and a density distribution map of retinal ganglion cells, and the generated data may be stored in the data storage unit 30.

The data may be used as comparison data during the future medical examination as well as the present medical examination data.

The retina and optic nerve function evaluation system 1 may further include a function information generation unit 40, and the function information generation unit 40 may receive a density distribution map (DM) and a retina image (RI) of retinal ganglion cells from the data storage unit 30, analyze them and generate retina and optic nerve function information. The retina and optic nerve function information may be information that can directly confirm the present state of the retina and optic nerve of the subject.

The retina and optic nerve function information may include the number of retinal ganglion cells of the present subject, the density distribution of the retinal ganglion cells and the number of abnormal retinal ganglion cells, and inform whether the number of cells and the density distribution of the present subject are within normal numerical ranges.

Further, the retina and optic nerve function information may be generated by comparing and analyzing previously generated retina image and density distribution map of retinal ganglion cells with the present retina image and density distribution map of retinal ganglion cells. That is, the retina and optic nerve function information may be generated by performing a regular checkup or the like once a year and may be provided by comparing and analyzing the states of the subject.

Further, the density distribution map of the retinal ganglion cells may separately indicate abnormal retinal ganglion cells. Information related to such abnormal retinal ganglion cells may be included in retina and optic nerve function information and enables early diagnosis of a disease based on the degree of increase in the number of the abnormal retinal ganglion cells.

Hereinafter, the retina and optic nerve function information outputting method according to an exemplary embodiment of the present invention will be described.

Figure 9:
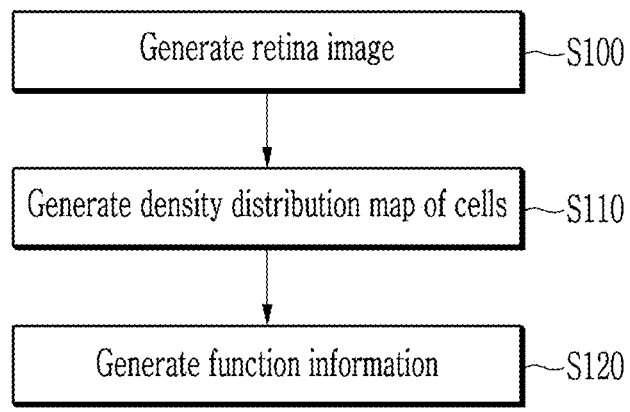
FIG. 9 is a flowchart of a method of outputting retina and optic nerve function information according to an exemplary embodiment of the present invention.

FIG. 9 is a flowchart showing a method of outputting retina and optic nerve function information according to an exemplary embodiment. Here, the retina and optic nerve function information outputting method according to an exemplary embodiment may be performed through the retina and optic nerve function evaluation system (1) as described above. Accordingly, reference may be made to FIGS. 1 to 4 and description thereof, and overlapping description will be omitted.

Referring to FIG. 9, a method of outputting retina and optic nerve function information according to an exemplary embodiment of the present invention includes generating a retina image by photographing an eyeball (S100), generating a density distribution map of retinal ganglion cells which indicates a distribution of retinal ganglion cells (S110), and generating function information (S120).

First, a retina image is generated (S100).

Generation of the retina image (RI) may be performed by the retina imaging unit 10. The retina imaging unit 10 may be configured of a differential interference microscope (DIC), and imaging of the transparent cells may be possible because imaging by interference is possible according to the occurrence of an optical distance difference.

Further, the retina imaging unit 10 may include a wavefront sensor and a light compensation mirror. The wavefront sensor may detect the aberration of light reflected from the eyeball and may analyze wavefronts distorted by the aberration. The light compensation mirror may compensate the light based on the aberration sensed by the wavefront sensor. The optical compensation mirror may be an adaptive mirror. That is, the retina imaging unit 10 which is applied with adaptive optics (AO) can compensate for the aberration generated due to the characteristics of the eyeball, enable imaging of retina nerve cells in vivo, and generate a retina image (RI) in which transparent retina cells are displayed.

Specifically, the retina imaging unit 10 can obtain at least one eyeground image at low magnification, obtain a plurality of DIC images of the retina of the entirety of at least one eyeground image obtained at high magnification, and generate the retina image (RI).

Next, the density distribution of retinal ganglion cells is generated (S110).

Retinal ganglion cells (RGC) and horizontal cells (AC) may be distinguished in consideration of the size, shape, etc. of the cells in the retina image (RI).

The retina image (RI) may be divided into subpixels of a predetermined size, cells larger than the subpixels may be classified as retinal ganglion cells (RGC), and cells smaller than the subpixels may be classified as horizontal cells. Further, the horizontal cells (AC) may be first selected in consideration of the fact that the edge that is the boundary region of the horizontal cells (AC) is displayed darker than the center region. That is, cells greater than a certain size in the remaining cells except the selected horizontal cells (AC) may be selected as retinal ganglion cells (RGC).

Here, the retina image (RI) may be an image obtained by photographing a specific region and may be provided in plurality. Each retina image (RI) may be selected for horizontal cells and retinal ganglion cells. The plurality of selected retina images (RI) may be combined into one image representing the entire retina, and based on the combined image, a density distribution map of retinal ganglion cells showing the distribution of retinal ganglion cells (RGC) may be generated according to the retina portion. However, the present invention is not limited thereto, the retina image (RI) may be a photographed image of the entire retina, and the density distribution map of the retinal ganglion cells may be generated by using the retina image (RI) provided by the retina imaging unit 10.

The density distribution map (DM) of the retinal ganglion cells may be generated by the cell density distribution generation unit 20.

The cell density distribution generation unit 20 may distinguish between normal retinal ganglion cells and abnormal retinal ganglion cells. Selected abnormal retinal ganglion cells may be subtracted from the number of normal retinal ganglion cells, but the present invention is not limited thereto and the abnormal retinal ganglion cells may be separately reflected into the density distribution map of the retinal ganglion cells.

Next, the function information is generated (S120).

The function information may be information that can directly provide the current retina and optic nerve state of the subject. The retina and optic nerve function information may be generated by analyzing a retina image (RI) and a density distribution map (DM) of the retinal ganglion cells. The retina and optic nerve function information may include at least the number of retinal ganglion cells, the density distribution of retinal ganglion cells and the number of abnormal retinal ganglion cells in the current patient, and inform whether the number of retinal ganglion cells and density distribution in the current patient are within normal numerical ranges. Such retina and optic nerve function information may be generated by the function information generation unit 40. The function information generation unit 40 may receive the density distribution map (DM) and retina image (RI) of retinal ganglion cells from the data storage unit 30, analyze them and generate retina and optic nerve function information.

Further, the retina and optic nerve function information may include data which have compared and analyzed previously generated retina image and density distribution map of retinal ganglion cells with the current retina image and density distribution map of retinal ganglion cells. That is, the retina and optic nerve function information may be generated by performing regular examinations, etc. once a year and may also provide a comparison and analysis of retina and optic nerve states of a subject.

The density distribution map of the retinal ganglion cells may separately indicate abnormal retinal ganglion cells. Information related to such abnormal retinal ganglion cells may be included in the retina and optic nerve function information, and enables early diagnosis of a optic nerve disease based on the degree of increase in the number of the abnormal retinal ganglion cells.

The method of outputting the retina and optic nerve function information may analyze the retina image and the density distribution map of the retinal ganglion cells and provide the subject with information on the retina and the optic nerve state.

The retina image is generated by photographing the retina of the subject, and the generation process thereof is temporary and does not directly affect the human body.

Further, the retina image can be generated precisely enough to visually distinguish the retinal ganglion cells from other cells, and their density distribution maps are automatically generated: even if it does not require a high level of medical instruction or experience from a physician, the subject can easily be provided with information on retina diseases.

Operations in the method of outputting the retina and optic nerve function information according to the exemplary embodiments as described above are at least partly implemented as a computer program and corresponding computer programs can be recorded on a computer-readable recording medium. The computer-readable recording medium having programs recorded thereon for implementing operations in the method of outputting retina and optic nerve function information according to exemplary embodiments includes all kinds of recording devices for storing data that can be read by a computer. Examples of computer-readable recording media include ROM, RAM, CD-ROM, magnetic tape, floppy disks, optical data storage devices, and the like. Further, the computer-readable recording medium can also be distributed over computer systems connected by networks so that the computer-readable codes are stored and executed in a distributed manner. In addition, functional programs, codes, and code segments for implementing the present embodiment will be readily understood by those skilled in the art to which the present embodiments belong.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS

1: Retina and optic nerve function evaluation system
10: Retina imaging unit
20: Cell density distribution generation unit
30: Data storage unit
40: Information generation unit

What is claimed is:
1. A retina imaging device comprising:
a light irradiation unit for irradiating two dispersed lights;
a magnification adjustment unit for adjusting the paths of the two lights and adjusting a magnification of an image obtained from the two lights incident on the eyeball, the magnification adjustment unit comprising:
a first lens on which the two dispersed lights are incident
a second lens on which the two lights that have passed through the first lens are incident; and
a third lens on which the two light that have passed through the second lens are incident, wherein the magnification of the image is defined according to a movement of the third lens such that a first movement of the third lens provides a first magnification and a second movement of the third lens provides a second magnification;
a light compensation unit for receiving lights reflected from the eyeball and compensating for aberrations of lights generated in the eyeball; and
a light processing unit comprising a charge-coupled device (CCD) that converts the compensated reflected lights into an electrical signal, the light processing unit configured for obtaining differential interference contrast (DIC) images by converting the electrical signal of the compensated reflected lights into a digital signal and image-processing the digital signal,
wherein the retina imaging device is configured to obtain at least one eyeground image at the first magnification, and obtain a plurality of DIC images at the second magnification higher than the first magnification with respect to the retina of the entirety of the obtained at least one eyeground image.
2. The retina imaging device of claim 1, wherein:
the magnification adjustment unit further includes:
a fixed frame to which the first lens and the second lens are fixed; and
an adjustment frame to which the third lens is fixed and whose position is moved with respect to the fixed frame.
3. The retina imaging device of claim 2, wherein:
the position of the third lens at the first magnification is farther from the eye than the position of the third lens at the second magnification.
4. The retina imaging device of claim 3, wherein:
at the first magnification, a region corresponding to the at least one eyeground image is specified by the two lights that have passed through the third lens and the lens of the eyeball, and
at the second magnification, a specific point of the region corresponding to the at least one eyeground image obtained by the two lights that have passed through the third lens and the lens of the eyeball is specified.
5. The retina imaging device of claim 1, wherein:
the light irradiation unit includes
a differential interference contrast (DIC) prism for dispersing a light to produce the two dispersed lights.
6. The retina imaging device of claim 5, wherein:
the two lights reflected from the eyeball are combined into one light in the DIC prism through the magnification adjustment unit and incident on the light compensation unit, and
wherein the light compensation unit includes
a wavefront sensor for detecting aberrations of the incident lights and
a variable mirror which is adjusted by the wavefront sensor for compensating for the aberrations of the incident lights.

* * * * *